United States Patent [19]

Rivier et al.

[11] Patent Number: 4,518,586

[45] Date of Patent: May 21, 1985

[54] GRF ANALOGS III

[75] Inventors: Jean E. F. Rivier; Wylie W. Vale, Jr., both of La Jolla, Calif.

[73] Assignee: The Salk Institute for Biological Studies, San Diego, Calif.

[21] Appl. No.: 545,094

[22] Filed: Oct. 25, 1983

Related U.S. Application Data

[63] Continuation-in-part of Ser. No. 532,170, Sep. 29, 1983, which is a continuation-in-part of Ser. No. 457,862, Jan. 13, 1983.

[51] Int. Cl.$^3$ .................. C07C 103/52; A61K 37/02
[52] U.S. Cl. ............................... 514/12; 260/112.5 R
[58] Field of Search ................... 260/112.5 R; 424/177

[56] References Cited

PUBLICATIONS

Science, Guillemin et al., "Growth Hormone–Releasing Factor from a Human Pancreatic Tumor that Caused Acromegaly", 11/5/82, vol. 218, pp. 585–587.
Nature, Spiess et al., "Characterization of Rat Hypothalamic Growth Hormone–Releasing Factor", vol. 303, Jun. 9, 1983, pp. 532–535.
8th American Peptide Symposium, Tucson, Arizona, May 22–27, 1983, p. 237, Abstract 10–B.
Biochemical and Biophysical Research Communications, Bohlen et al., "Isolation and Characterization of the Porcine Hypothalamic Growth Hormone Releasing Factor, vol. 116, No. 2, 1983, Oct. 31, 1983.
J. Spiess et al., *Biochemistry*, 21, 6037–6040, (1982).
F. S. Esch et al., *Biochemical* and *Biophysical Research Communications*, 109, No. 1, 152–158, (1982).
F. S. Esch et al., *The Journal of Biological Chemistry*, 258, No. 3, 1806–1810, (1983), Feb. 10 issue.

*Primary Examiner*—Delbert R. Phillips
*Assistant Examiner*—F. T. Moezie

*Attorney, Agent, or Firm*—Fitch, Even, Tabin & Flannery

[57] ABSTRACT

Human parcreatic GRF(hpGRF), rat hypothalamic GRF(rGRF) and porcine hypothalamic GRF(pGRF) have been earlier characterized and synthesized. The invention provides synthetic peptides which are extremely potent in stimulating the release of pituitary GH in animals, including humans, which have resistance to enzymatic degradation in the body, and which have the sequence: $R_1$-$R_2$-$R_3$-Ala-Ile-Phe-Thr-$R_8$-Ser-$R_{10}$-Arg-$R_{12}$-$R_{13}$-Leu-$R_{15}$-Gln-$R_{17}$-$R_{18}$-Ala-Arg-Lys-Leu-$R_{23}$-$R_{24}$-$R_{25}$-Ile-$R_{27}$-$R_{28}$-Arg-Gln-Gln-Gly-Glu-$R_{34}$-Asn-Gln-Glu-$R_{38}$-$R_{39}$-$R_{40}$-Arg-$R_{42}$-$R_{43}$-$R_{44}$ wherein $R_1$ is Tyr, D-Tyr, Met, Phe, D-Phe, pCl-Phe, Leu, His or D-His having either a C$^\alpha$Me or N$^\alpha$Me substitution or being unsubstituted; $R_2$ is Ala or D-Ala; $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, Asp, D-Glu or D-Asp; $R_{27}$ is Met, D-Met, Ala, Nle, Ile, Leu, Nva or Val; $R_{28}$ is Asn or Ser; $R_{34}$ is Arg or Ser; $R_{38}$ is Gln or Arg; $R_{39}$ is Arg or Gly; $R_{40}$ is Ser or Ala; $R_{42}$ is Phe, Ala or Val; $R_{43}$ is Asn or Arg; $R_{44}$ is a natural amino acid; provided however that either $R_{17}$ or $R_{23}$ is D-Leu or $R_{25}$ is either D-Glu or D-Asp and that any or all of the residues between $R_{29}$ and $R_{44}$, inclusive, may be deleted; or a nontoxic salt thereof. The carboxyl moiety of the amino acid residue at the C-terminus can be the radical —COOR,—CRO,—CONHNHR,—CON(R)(R') or —CH$_2$OR, with R and R' being lower alkyl, fluoro lower alkyl or hydrogen. These peptides as well as nontoxic salts thereof may be administered to animals, including humans and cold-blooded animals, to stimulate the release of GH and may be used diagnostically.

20 Claims, No Drawings

GRF ANALOGS III

This invention was made with Government support under Grant No. AM-26741 awarded by the National Institutes of Health. The Government has certain rights in this invention.

This application is a continuation-in-part of Ser. No. 532,170, 9/29/83, which is a continuation-in-part of Ser. No. 457,862 (Jan. 13, 1983).

The present invention relates to peptides having influence on the function of the pituitary gland in humans and other animals. In particular, the present invention is directed to a peptide which promotes the release of growth hormone by the pituitary gland.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. Hypothalamic releasing factors have been characterized for the pituitary hormones thyrotropin and prolactin (the tripeptide TRF), for the pituitary gonadotropins luteinizing hormone and follicle stimulating hormone (the decapeptide LRF, LH-RH or GnRH) and for the pituitary hormones β-endorphin and adrenocorticotropin (the 41-amino acid polypeptide CRF). An inhibitory factor has also been characterized in the form of somatostatin which inhibits the secretion of growth hormone (GH). In 1982, human pancreatic (tumor) releasing factors (hpGRF) were isolated from extracts of human pancreatic tumors, purified, characterized, synthesized and tested, which were found to promote the release of GH by the pituitary. Each of these hypophysiotropic factors has been reproduced by total synthesis, and analogs of the native structures have been synthesized. A corresponding rat hypothalamic GH releasing factor (rGRF) and a corresponding porcine hypothalamic GH releasing factor (pGRF) have also been characterized and synthesized.

SUMMARY OF THE INVENTION

Synthetic polypeptides have now been synthesized and tested which release GH from cultured pituitary cells and which may at least partially resist enzymatic degradation in the body. These peptides have D-Leu in the 17- and/or 23-positions and/or D-Glu or D-Asp in the 25-position; the peptides may also have one of the following residues in the 1-position: Tyr, D-Tyr, Met, Phe, D-Phe, pCl-Phe, Leu, His and D-His, which residue may optionally have a methyl substitution either on the alpha-carbon or in the alpha amino group. They may optionally have D-Ala at the 2-position and/or D-Asp at the 3-position and/or D-Arg or D-Ser at the 8-position and/or D-Tyr at the 10-position and/or D-Ala at the 15-position. They preferably also have a substitution such as D-Met, Nle or Nva for Met in the 27-position.

Pharmaceutical compositions in accordance with the invention include such analogs which are between about 28 and 44 residues in length, or a nontoxic salt of any of these, dispersed in a pharmaceutically or veterinarily acceptable liquid or solid carrier. Such pharmaceutical compositions can be used in clinical medicine, both human and veterinary, for administration for therapeutic purposes, and also diagnostically. Moreover, they can be used to promote the growth of warm-blooded animals, including fowl, and in aquiculture for cold-blooded animals, e.g. fish, eels, etc.

DETAILED DESCRIPTION OF PREFERRED EMBODIMENTS

The nomenclature used to define the peptides is that specified by Schroder and Lubke, "The Peptides", Academic Press (1965), wherein in accordance with conventional representation the amino group at the N-terminus appears to the left and the carboxyl group at the C-terminus to the right. By natural amino acid is meant one of common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. By Nle is meant norleucine, and by Nva is meant norvaline. When the amino acid residue has isomeric forms, it is the L-form of the amino acid that is represented unless otherwise expressly indicated.

The invention provides synthetic peptides having the following sequence: H-$R_1$-$R_2$-$R_3$-Ala-Ile-Phe-Thr-$R_8$-Ser-$R_{10}$-Arg-$R_{12}$-$R_{13}$-Leu-$R_{15}$-Gln-$R_{17}$-$R_{18}$-Ala-Arg-Lys-Leu-$R_{23}$-$R_{24}$-$R_{25}$-Ile-$R_{27}$-$R_{28}$-Arg-Gln-Gln-Gly-Glu-$R_{34}$-Asn-Gln-Glu-$R_{38}$-$R_{39}$-$R_{40}$-Arg-$R_{42}$-$R_{43}$-$R_{44}$ wherein $R_1$ is Tyr, D-Tyr, Met, Phe, D-Phe, pCl-Phe, Leu, His or D-His having either a $C^\alpha$Me or $N^\alpha$Me substitution or being unsubstituted; $R_2$ is Ala or D-Ala, $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, D-Glu, D-Asp or Asp; $R_{27}$ is Met, D-Met, Ala, Nle, Ile, Leu, Nva or Val; $R_{28}$ is Asn or Ser; $R_{34}$ is Arg or Ser; $R_{38}$ is Gln or Arg; $R_{39}$ is Arg or Gly; $R_{40}$ is Ser or Ala; $R_{42}$ is Phe, Ala or Val; $R_{43}$ is Asn or Arg; $R_{44}$ is a natural amino acid; provided however that any or all of the residues between $R_{29}$ and $R_{44}$, inclusive, may be deleted and that $R_{17}$ or $R_{23}$ is D-Leu or $R_{25}$ is either D-Glu or D-Asp. The carboxyl moiety of the amino acid residue at the C-terminus is preferably "Y" which represents the radical —COOR, —CRO, —CONHNHR, —CON(R)(R') or —CH$_2$OR, with R and R' being lower alkyl, fluoro lower alkyl or hydrogen; methyl, ethyl and propyl are the preferred lower alkyl groups. Usually when a residue is included in the 44-position, an amino acid other than Cys is chosen unless there would be a desire to form a dimer or link the synthetic peptide to another peptide. When Met appears in position 1, it may be preferable to have another residue in position 27.

As defined above, fragments which extend from the N-terminal through residue-28 have biological potency, and such biologically active fragments are considered as falling within the scope of the overall invention. When the peptide fragment extends only to residue 28, Y should be NH$_2$ or a substituted amide. When the fragment extends to one of residues 29 thru 39, Y is preferably an amide or a substituted amide but may be OH. When the fragment has 40 or more residues, there is no clear preference for the moiety at the C-terminus.

The peptides are synthesized by a suitable method, such as by exclusively solid-phase techniques, by partial solid-phase techniques, by fragment condensation or by classical solution couplings. The employment of recently developed recombinant DNA techniques may be used to prepare a portion of an analog containing only natural amino acid residues. For example, the techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula: $X^1$-$R_1$(X or $X^2$)-$R_2$-$R_3$($X^3$)-Ala-Ile-Phe-Thr($X^4$)-$R_8$($X^4$ or $X^5$)-Ser($X^4$)-$R_{10}$($X^2$)-Arg($X^6$)-$R_{12}$($X^6$ or $X^7$)-$R_{13}$-Leu-$R_{15}$-Gln($X^5$)-$R_{17}$-$R_{18}$($X^2$)-Ala-Arg($X^6$)-Lys($X^7$)-Leu-$R_{23}$-$R_{24}$(X or $X^5$)-$R_{25}$($X^3$)-Ile-$R_{27}$-$R_{28}$($X^4$ or $X^5$)-Arg($X^6$)-Gln($X^5$)-Gln($X^5$)-Gly-Glu($X^3$)-$R_{34}$($X^4$ or $X^6$)-Asn($X^5$)-Gln($X^5$)-Glu($X^3$)-$R_{38}$($X^5$ or $X^6$)-$R_{39}$($X^6$)-$R_{40}$($X^4$)-Arg($X^6$)-$R_{42}$-$R_{43}$($X^5$ or $X^6$)-$R_{44}$($X^8$)-$X^9$ wherein: $X^1$ is either hydrogen or an α-amino protecting group. The α-amino protecting groups contemplated by $X^1$ are those well known to be useful in the art of step-wise synthesis of polypeptides. Among the classes of α-amino protecting groups which may be employed as $X^1$ are (1) aromatic urethan-type protecting groups, such as fluorenylmethyloxycarbonyl (FMOC), benzyloxycarbonyl(Z) and substituted Z, such as p-chlorobenzyloxycarbonyl, p-nitrobenzyloxycarbonyl, p-bromobenzyloxycarbonyl, and p-methoxybenzyloxycarbonyl; (2) aliphatic urethan protecting groups, such as t-butyloxycarbonyl (BOC), diisopropylmethyloxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl, and cyclohexyloxycarbonyl. The preferred α-amino protecting group is BOC, even when an $N^\alpha$Me-substituted residue is employed in the 1-position.

X is hydrogen or a protecting group for the imidazole nitrogen of His, such as Tos.

$X^2$ may be a suitable protecting group for the phenolic hydroxyl group of Tyr, such as tetrahydropyranyl, tert-butyl, trityl, Bzl, CBZ, 4Br-CBZ and 2,6-dichlorobenzyl (DCB). The preferred protecting group is 2,6-dichlorobenzyl. $X^2$ can be hydrogen which means that there is no side-chain protecting group on the amino acid residue in that position.

$X^3$ is hydrogen or a suitable ester-forming protecting group for the carboxyl group of Asp or Glu, such as benzyl (OBzl), 2,6-dichlorobenzyl, methyl and ethyl.

$X^4$ may be a suitable protecting group for the hydroxyl group of Thr or Ser, such as acetyl, benzoyl, tert-butyl, trityl, tetrahydropyranyl, Bzl, 2,6-dichlorobenzyl and CBZ. The preferred protecting group is Bzl. $X^4$ can be hydrogen, which means there is no protecting group on the hydroxyl group.

$X^5$ is hydrogen or a suitable protecting group for the side chain amido group of Asn or Gln. It is preferably xanthyl (Xan).

$X^6$ is a suitable protecting group for the guanidino group of Arg, such as nitro, Tos, CBZ, adamantyloxycarbonyl, and BOC, or is hydrogen.

$X^7$ is hydrogen or a suitable protecting group for the side chain amino group of Lys. Illustrative of suitable side chain amino protecting groups are 2-chlorobenzyloxycarbonyl (2-Cl-Z), Tos, t-amyloxycarbonyl and BOC.

$X^8$ is hydrogen or a suitable side-chain protecting group is generally specified above.

Met can optionally be protected by oxygen, but is preferably left unprotected.

The selection of a side chain amino protecting group is not critical except that generally one is chosen which is not removed during deprotection of the α-amino groups during the synthesis. However, for some amino acids, e.g. His, protection is not generally necessary after coupling is completed, and the protecting groups may be the same.

$X^9$ is a suitable protecting group for the C-terminal carboxyl group, such as the ester-forming group $X^3$, or is an anchoring bond used in solid-phase synthesis for linking to a solid resin support, or is des-$X^9$, in which case the residue at the C-terminal has a carboxy moiety which is Y, as defined hereinbefore. When a solid resin support is used, it may be any of those known in the art, such as one having the formulae: —O—CH$_2$-resin support, —NH-benzhydrylamine (BHA) resin support or —NH-paramethylbenzhydrylamine (MBHA) resin support. When the unsubstituted amide is desired, use of BHA or MBHA resin is preferred, because cleavage directly gives the amide. In case the N-methyl amide is desired, it can be generated from an N-methyl BHA resin. Should other substituted amides be desired or should other groups than the free acid be desired at the C-terminus, it may be preferable to synthesize the peptide using classical methods as set forth in the Houben-Weyl text.

In the formula for the intermediate, at least one of the X-groups is a protecting group or $X^9$ includes resin support. Thus, the invention also provides a method for manufacturing a peptide of interest by (a) forming a peptide having at least one protective group and the formula (II): $X^1$-$R_1$(X or $X^2$)-$R_2$-$R_3$($X^3$)-Ala-Ile-Phe-Thr($X^4$)-$R_8$($X^4$ or $X^5$)-Ser($X^4$)-Tyr($X^2$)-Arg($X^6$)-$R_{12}$($X^6$ or $X^7$)-$R_{13}$-Leu-Gly-Gln($X^5$)-$R_{17}$-$R_{18}$($X^2$)-Ala-Arg($X^6$)-Lys($X^7$)-Leu-$R_{23}$-$R_{24}$(X or $X^5$)-$R_{25}$($X^3$)-Ile-$R_{27}$-$R_{28}$($X^4$ or $X^5$)-Arg($X^6$)-Gln($X^5$)-Gln($X^5$)-Gly-Glu($X^3$)-$R_{34}$($X^4$ or $X^6$)-Asn($X^5$)-Gln($X^5$)-Glu($X^3$)-$R_{38}$($X^5$ or $X^6$)-$R_{39}$($X^6$)-$R_{40}$($X^4$)-Arg($X^6$)-$R_{42}$-$R_{43}$($X^5$ or $X^6$)-$R_{44}$($X^8$)-$X^9$ wherein: X, $X^1$, $X^2$, $X^3$, $X^4$, $X^5$, $X^6$, $X^7$ and $X^8$ are each either hydrogen or a protective group and $X^9$ is either a protective group or an anchoring bond to resin support or des-$X^9$, in which case the residue at the C-terminal has a carboxy moiety which is Y; (b) splitting off the protective group or groups or anchoring bond from said peptide of the formula (II); and (c) if desired, converting a resulting peptide into a nontoxic salt thereof.

In selecting a particular side chain protecting group to be used in the synthesis of the peptides, the following general rules are followed: (a) the protecting group preferably retains its protecting properties and is not split off under coupling conditions, (b) the protecting group should be stable to the reagent and, with the exception of Xan, is preferably stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

When peptides are not prepared using recombinant DNA technology, they are preferably prepared using solid phase synthesis, such as that generally described by Merrifield, *J. Am. Chem. Soc.*, 85, p 2149 (1963), although other equivalent chemical syntheses known in the art can also be used as previously mentioned. Solid-phase synthesis is commenced from the C-terminal end of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6. BHA and MBHA resin supports are commercially available and are generally used only when the desired polypeptide being synthesized has an unsubstituted amide at the C-terminal.

The C-terminal amino acid, i.e. Asn, protected by BOC and by Xan, can be first coupled to the chloromethylated resin according to the procedure set forth in *Chemistry Letters*, K. Horiki et al. 165-168 (1978), using KF in DMF at about 60° C. for 24 hours with stirring, when the 43-residue peptide is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder and Lubke, "The Peptides", 1 pp 72-75 (Academic Press 1965).

After removal of the α-amino protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder and Lubke supra, in Chapter III and by Kapoor, *J. Phar. Sci.*, 59, pp 1-27 (1970).

Each protected amino acid or amino acid sequence is introduced into the solid phase reactor in about a four-fold or more excess, and the coupling may be carried out in a medium of dimethylformamide (DMF): $CH_2Cl_2$ (1:1) or in DMF or $CH_2Cl_2$ alone. In cases where incomplete coupling occurs, the coupling procedure is repeated before removal of the α-amino protecting group prior to the coupling of the next amino acid. The success of the coupling reaction at each stage of the synthesis, is performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers*, 1978, 17, pp 1927-1938.

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups X, $X^2$, $X^3$, $X^4$, $X^5$, $X^6$, $X^7$ and $X^8$ and the anchoring bond $X^9$ and also the α-amino protecting group $X^1$ if one is used, to obtain the peptide in the form of the free acid. If Met is present in the sequence, the BOC protecting group is preferably first removed using trifluoroacetic acid (TFA)/ethanedithiol prior to cleaving the peptide from the resin with HF to eliminate potential S-alkylation. When using hydrogen fluoride for cleaving, anisole and methylethyl sulfide are included as scavengers in the reaction vessel.

The following Example sets forth a preferred method for synthesizing peptides by the solid-phase technique. It will of course be appreciated that the synthesis of a correspondingly shorter peptide fragment is effected in the same manner by merely eliminating the requisite number of amino acids at either end of the chain; however, it is presently felt that biologically active fragments should contain the indicated sequence at the N-terminus.

The structure of native rGRF is set forth in commonly assigned copending U.S. patent application Ser. No. 488,748 filed Apr. 26, 1983, the disclosure of which is incorporated herein by reference.

EXAMPLE I

The synthesis of the peptide [N$^\alpha$MeTyr$^1$, D-Leu$^{23}$]-rGRF(1-43)-OH having the formula: N$^\alpha$MeTyr-Ala-Asp-Ala-Ile-Phe-Thr-Ser-Ser-Tyr-Arg-Arg-Ile-Leu-Gly-Gln-Leu-Tyr-Ala-Arg-Lys-Leu-D-Leu-His-Glu-Ile-Met-Asn-Arg-Gln-Gln-Gly-Glu-Arg-Asn-Gln-Glu-Gln-Arg-Ser-Arg-Phe-Asn-OH is conducted in a stepwise manner using a Beckman 990 peptide synthesizer on a chloromethylated resin having a substitution range of about 0.1 to 0.5 mmoles/g. resin. Coupling of BOC-Asn(Xan) to the resin is performed by the general procedure set forth in *Chemistry Letters*, supra, using KF in DMF at about 60° C. for 24 hours with stirring, and it results in the substitution of about 0.35 mmol. Asn per gram of resin.

After deblocking and neutralization, the peptide chain is built step-by-step on the resin. Deblocking, neutralization and addition of each amino acid is performed in general accordance with the procedure set forth in detail in Rivier, J, *J. Amer. Chem. Soc.*, 96, 2986-2992 (1974). All solvents that are used are carefully degassed by sparging with an inert gas, e.g. helium or nitrogen, to insure the absence of oxygen that might undesirably oxidize the sulfur of the Met residue.

Deblocking is preferably carried out in accordance with Schedule A which follows:

SCHEDULE A

| Reagent | Mixing time (Min.) |
| --- | --- |
| 1. 60% TFA/2% ethanedithiol | 10 |
| 2. 60% TFA/2% ethanedithiol | 15 |
| 3. IPA/1% ethanedithiol | 0.5 |
| 4. Et$_3$N (10%) in CH$_2$Cl$_2$ | 0.5 |
| 5. MeOH | 0.5 |
| 6. Et$_3$N (10%) in CH$_2$Cl$_2$ | 0.5 |
| 7. MeOH (twice) | 0.5 |
| 8. CH$_2$Cl$_2$ (twice) | 0.5 |

The couplings are preferably carried out as set out in Schedule B which follows:

SCHEDULE B

| Reagent | Mixing time (Min.) |
| --- | --- |
| 9. DCCI | — |
| 10. Boc-amino acid | 50–90 |
| 11. MeOH (twice) | 0.5 |
| 12. CH$_2$Cl$_2$ (twice) | 0.5 |
| 13. Ac$_2$O (3 M) in CH$_2$Cl$_2$ | 15.0 |
| 14. CH$_2$Cl$_2$ | 0.5 |
| 15. MeOH | 0.5 |
| 16. CH$_2$Cl$_2$ (twice) | 0.5 |

Briefly, one to two mmol. of BOC-protected amino acid in methylene chloride is used per gram of resin, plus one equivalent of 1.0 molar DCCI in methylene chloride for two hours. When BOC-Arg(TOS) is being coupled, a mixture of 50% DMF and methylene chloride is used. Bzl ether is used as the hydroxyl side-chain protecting group for Ser and Thr. The amido group of Asn or Gln is protected by Xan when DCC coupling is used as is preferred. P-nitrophenyl ester (ONp) may also be used to activate the carboxyl end of Asn or Gln, and for example, BOC-Asn(ONp) can be coupled overnight using one equivalent of HOBt in a 50% mixture of DMF and methylene chloride, in which case no DCC is added. 2-chloro-benzyloxycarbonyl (2Cl-Z) is used as the protecting group for the Lys side chain. Tos is used to protect the guanidino group of Arg and the imidazole nitrogen of His, and the Glu or Asp side-chain carboxyl group is protected with OBzl. The phenolic hydroxyl group of Tyr is protected with 2,6-dichlorobenzyl (DCB). At the end of the synthesis, the following composition is obtained: BOC-N$^\alpha$MeTyr(X$^2$)-Ala-Asp(X$^3$)-Ala-Ile-Phe-Thr(X$^4$)-Ser(X$^4$)-Ser(X$^4$)-Tyr(X$^2$)-Arg(X$^6$)-Arg(X$^6$)-Ile-Leu-Gly-Gln(X$^5$)-Leu-Tyr(X$^2$)-Ala-Arg(X$^6$)-Lys(X$^7$)-Leu-D-Leu-His(X)-Glu(X$^3$)-Ile-Met-Asn(X$^5$)-Arg(X$^6$)-Gln(X$^5$)-Gln(X$^5$)-Gly-Glu(X$^3$)-Arg(X$^6$)-Asn(X$^5$)-Gln(X$^5$)-Glu(X$^3$)-Gln(X$^6$)-Ser(X$^4$)-Arg(X$^6$)-Phe-Asn(X$^5$)-X$^9$ wherein X$^2$ is DCB, X$^3$ is OBzl, X$^4$ is Bzl, X$^5$ is Xan, X$^6$ is Tos, X$^7$ 2Cl-Z and X$^9$ is —O—CH$_2$-resin support. Xan may have been partially or totally removed by TFA treatment used to deblock the α-amino protecting group.

In order to cleave and deprotect the protected peptide-resin, it is treated with 1.5 ml. anisole, 0.5 ml. methylethylsulfide and 15 ml. hydrogen fluoride (HF) per gram of peptide-resin, at −20° C. for one-half hour and at 0.° C. for one-half hour. After elimination of the HF under high vacuum, the resin-peptide remainder is washed alternately with dry diethyl ether and chloroform, and the peptide is then extracted with degassed 2N aqueous acetic acid and separated from the resin by filtration.

The cleaved and deprotected peptide is then dissolved in 0–5% acetic acid and subjected to purification which may include Sephadex G-50 fine gel filtration.

The peptide is then further purified by preparative or semi-preparative HPLC as described in Rivier et al., *Peptides: Structure and Biological Function*, (1979) pp 125–8 and Marki et al. *J. Am. Chem. Soc.* 103, 3178 (1981). Cartridges fitting Waters Associates prep LC-500 are packed with 15–20μ C$_{18}$ Silica from Vydac (300A). A gradient of CH$_3$CN in TEAP is generated by a low pressure Eldex gradient maker, as described in Rivier, J., *J. Liq. Chromatography* 1, 343–367 (1978). The chromatographic fractions are carefully monitored by HPLC, and only the fractions showing substantial purity are pooled. Desalting of the purified fractions, independently checked for purity, is achieved using a gradient of CH$_3$CN in 0.1% TFA. The center cut is then lyophilized to yield the desired peptide, the purity of which can be greater than 98%.

The synthesis is repeated using an MBHA resin to produce the same peptide having an amidated C-terminus using an initial procedure as generally described in Vale et al. U.S. Pat. No. 4,292,313 to link ASN to the MBHA resin.

EXAMPLE II

The synthesis of a 40-residue amidated peptide [C$^\alpha$MeHis$^1$, D-Leu$^{23}$]-hpGRF(1–40)-NH$_2$ having the formula: H-C$^\alpha$-MeHis-Ala-Asp-Ala-Ile-Phe-Thr-Asn-Ser-Tyr-Arg-Lys-Val-Leu-Gly-Gln-Leu-Ser-Ala-Arg-Lys-Leu-D-Leu-Gln-Asp-Ile-Met-Ser-Arg-Gln-Gln-Gly-Glu-Ser-Asn-Gln-Glu-Arg-Gly-Ala-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE III

The synthesis of [N$^\alpha$Me-Met$^1$, D-Leu$^{23}$, Nle$^{27}$]-rGRF(1–43)-OH having the formula: N$^\alpha$MeMet-Ala-Asp-Ala-Ile-Phe-Thr-Ser-Ser-Tyr-Arg-Arg-Ile-Leu-Gly-Gln-Leu-Tyr-Ala-Arg-Lys-Leu-D-Leu-His-Glu-Ile-Nle-Asn-Arg-Gln-Gln-Gly-Glu-Arg-Asn-Gln-Glu-Gln-Arg-Ser-Arg-Phe-Asn-OH is conducted in a stepwise manner using a Beckman 990 Peptide Synthesizer on a chloromethylated resin, in the manner generally described in Example I. The peptide is judged to be substantially pure using TLC and HPLC.

EXAMPLE IV

The synthesis of a hpGRF analog fragment, i.e. [D-Leu$^{23}$]-hpGRF(1–32)-NH$_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-D-Leu-Gln-Asp-Ile-Met-Ser-Arg-Gln-Gln-Gly-NH$_2$ is conducted in a stepwise manner using a Beckman 990 Peptide Synthesizer on an MBHA resin as in Example II. This analog is judged to be substantially pure using TLC and HPLC.

The synthesis is repeated twice to produce [D-Leu$^{23}$, D-Glu$^{25}$]-hpGRF(1–32)-NH$_2$ and [D-Leu$^{23}$, Nle$^{27}$]-hpGRF(1–32)-NH$_2$.

EXAMPLE V

The synthesis of a hpGRF analog fragment i.e. [D-Leu$^{23}$, D-Asp$^{25}$, Nle$^{27}$]-hpGRF(1-29)-NH$_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-D-Leu-Gln-D-Asp-Ile-Nle-Ser-Arg-NH$_2$ is conducted in a stepwise manner using a Beckman 990 Peptide Synthesizer on an MBHA resin as in Example II. The peptide is judged to be substantially pure using TLC and HPLC.

EXAMPLE VI

The synthesis of [D-Leu$^{23}$, Nle$^{27}$]-rGRF(1-29)-NH$_2$, having the formula: H-His-Ala-Asp-Ala-Ile-Phe-Thr-Ser-Ser-Tyr-Arg-Arg-Ile-Leu-Gly-Gln-Leu-Tyr-Ala-Arg-Lys-Leu-D-Leu-His-Glu-Ile-Nle-Asn-Arg-NH$_2$ is conducted in a stepwise manner using a Beckman 990 Peptide Synthesizer on an MBHA resin as in Example II. The peptide is judged to be substantially pure using TLC and HPLC.

The synthesis is repeated to produce [D-Leu$^{17}$, Nle$^{27}$]-rGRF(1-29)-NH$_2$.

EXAMPLE VII

The synthesis of [D-Glu$^{25}$,Nle$^{27}$]-hpGRF(1-29)-NH$_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-D-Glu-Ile-Nle-Ser-Arg-NH$_2$ is conducted in a stepwise manner using a Beckman 990 Peptide Synthesizer on an MBHA resin as in Example II. The peptide is judged to be substantially pure using TLC and HPLC.

EXAMPLE VIII

The synthesis of [D-Glu$^{25}$, Nle$^{27}$]-rGRF(1-29)-NH$_2$ having the formula: H-His-Ala-Asp-Ala-Ile-Phe-Thr-Ser-Ser-Tyr-Arg-Arg-Ile-Leu-Gly-Gln-Leu-Tyr-Ala-Arg-Lys-Leu-Leu-His-D-Glu-Ile-Nle-Asn-Arg-NH$_2$ is conducted in a stepwise manner using a Beckman 990 Peptide Synthesizer on an MBHA resin as in Example II. The peptide is judged to be substantially pure using TLC and HPLC.

EXAMPLE IX

The synthesis of [D-Tyr$^1$, D-Leu$^{23}$]-pGRF(1-44)-NH$_2$ having the formula: H-D-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-D-Leu-Gln-Asp-Ile-Met-Ser-Arg-Gln-Gln-Gly-Glu-Arg-Asn-Gln-Glu-Gln-Gly-Ala-Arg-Val-Arg-Leu-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE X

The synthesis of [D-His$^1$, D-Leu$^{17, 23}$, D-Glu$^{25}$, Nle$^{27}$]-rGRF(1-43)-OH having the formula: H-D-His-Ala-Asp-Ala-Ile-Phe-Thr-Ser-Ser-Tyr-Arg-Arg-Ile-Leu-Gly-Gln-D-Leu-Tyr-Ala-Arg-Lys-Leu-D-Leu-His-D-Glu-Ile-Nle-Asn-Arg-Gln-Gln-Gly-Glu-Arg-Asn-Gln-Glu-Gln-Arg-Ser-Arg-Phe-Asn-OH is conducted in a stepwise manner using a Beckman 990 Peptide Synthesizer on a chloromethylated resin, in the manner generally described in Example I. The peptide is judged to be substantially pure using TLC and HPLC.

EXAMPLE XI

The synthesis of [D-Ala$^2$, D-Leu$^{17, 23}$, D-Asp$^{25}$]-hpGRF(1-32)-NH$_2$ having the formula: H-Tyr-D-Ala-Asp-Ala-Ile-Phe-Thr-Asn-Ser-Tyr-Arg-Lys-Val-Leu-Gly-Gln-D-Leu-Ser-Ala-Arg-Lys-Leu-D-Leu-Gln-D-Asp-Ile-Met-Ser-Arg-Gln-Gln-Gly-NH$_2$ is conducted in a stepwise manner using a Beckman 990 Peptide Synthesizer on an MBHA resin as in Example II. This analog is judged to be substantially pure using TLC and HPLC.

EXAMPLE XII

The synthesis of [D-Tyr$^1$, D-Ala$^2$, D-Asp$^3$, D-Asn$^8$, D-Tyr$^{10}$, D-Ala$^{15}$, D-Leu$^{17,23}$, D-Asp$^{25}$, D-Met$^{27}$]-hpGRF(1-29)-NH$_2$ having the formula: H-D-Tyr-D-Ala-D-Asp-Ala-Ile-Phe-Thr-D-Asn-Ser-D-Tyr-Arg-Lys-Val-Leu-D-Ala-Gln-D-Leu-Ser-Ala-Arg-Lys-Leu-D-Leu-Gln-D-Asp-Ile-D-Met-Ser-Arg-NH$_2$ is conducted in a stepwise manner using a Beckman 990 Peptide Synthesizer on an MBHA resin as in Example II. This analog is judged to be substantially pure using TLC and HPLC.

EXAMPLE XIII

The synthesis of [D-His$^1$, D-Ser$^8$, D-Leu$^{23}$, Nle$^{27}$]-rGRF(1-43)-OH having the formula: H-D-His-Ala-Asp-Ala-Ile-Phe-Thr-D-Ser-Ser-Tyr-Arg-Arg-Ile-Leu-Gly-Gln-Leu-Tyr-Ala-Arg-Lys-Leu-D-Leu-His-Glu-Ile-Nle-Asn-Arg-Gln-Gln-Gly-Glu-Arg-Asn-Gln-Glu-Gln-Arg-Ser-Arg-Phe-Asn-OH is conducted in a stepwise manner using a Beckman 990 Peptide Synthesizer on a chloromethylated resin, in the manner generally described in Example I. The peptide is judged to be substantially pure using TLC and HPLC.

EXAMPLE XIV

The synthesis of a rGRF analog fragment i.e. [N$^\alpha$Me-Tyr$^1$, D-Glu$^{25}$]-rhGRF(1-29)-NH$_2$ having the formula: N$^\alpha$MeTyr-Ala-Asp-Ala-Ile-Phe-Thr-Ser-Ser-Tyr-Arg-Arg-Ile-Leu-Gly-Gln-Leu-Tyr-Ala-Arg-Lys-Leu-Leu-His-D-Glu-Ile-Met-Asn-Arg-NH$_2$ is conducted in a stepwise manner using a Beckman 990 Peptide Synthesizer on an MBHA resin as in Example II. The peptide is judged to be substantially pure using TLC and HPLC.

EXAMPLE XV

The synthesis of [C$^\alpha$MeLeu$^1$, D-Leu$^{23}$, D-Glu$^{25}$, Nle$^{27}$]-rGRF-[Val$^{44}$]-NH$_2$ having the formula: H-C$^\alpha$MeLeu-Ala-Asp-Ala-Ile-Phe-Thr-Ser-Ser-Tyr-Arg-Arg-Ile-Leu-Gly-Gln-Leu-Tyr-Ala-Arg-Lys-Leu-D-Leu-His-D-Glu-Ile-Nle-Asn-Arg-Gln-Gln-Gly-Glu-Arg-Asn-Gln-Glu-Gln-Arg-Ser-Arg-Phe-Asn-Val-NH$_2$ is conducted in a stepwise manner using a Beckman 990 Peptide Synthesizer on an MBHA resin as in Example II. The peptide is judged to be substantially pure using TLC and HPLC.

Various of the synthetic peptides prepared in the Examples are compared with synthetic hpGRF(1-40)-OH in in vitro assays and are found to exhibit generally greater potencies for the secretion of GH and similar intrinsic activities.

To determine the effectiveness of the various synthetic peptides to promote the release of growth hormone, in vitro assays are carried out using synthetic hpGRF(1-40)-OH as a standard in side-by-side comparison with equimolar concentrations of the various other analogs and fragments synthesized. Cultures are used which include cells of rat pituitary glands removed some three to five days previously. Cultures which are considered optimal for the secretion of growth hormone are used for the comparative testing, in the general manner described in Vale et al. *Endocrinology*, 91, 562–572 (1972) and as more particularly described in Vale et al. Endocrinology, (1983), in press. Incubation with the substance to be tested is carried out for 3 to 4 hours, and aliquots of the culture medium are removed and processed to measure their contents in immunoreactive GH(ir GH) by a well-characterized radioimmunoassay.

The results of this comparative testing for equimolar concentrations are shown in Table I.

TABLE I

| Peptide | Comparison % |
|---|---|
| hpGRF(1-40)-OH (standard for this test) | 100% |
| [D-Glu$^{25}$, Nle$^{27}$]-rGRF(1-29)-NH$_2$ | 125% |
| [D-Leu$^{23}$, Nle$^{27}$]-rGRF(1-29)-NH$_2$ | 160% |
| [D-Leu$^{17}$, Nle$^{27}$]-rGRF(1-29)-NH$_2$ | 138% |

In vitro testing of these synthetic peptides shows that they each have the full intrinsic biological activity of hpGRF(1-40)-OH. THe maximum effective concentration for [D-Leu$^{23}$, Nle$^{27}$]-hpGRF(1-29)-NH$_2$ is about 1 nanomolar.

In addition to the in vitro tests for secretion of growth hormone, in vivo experiments inject the synthetic peptides through an indwelling catheter into freely running normal male rats after pretreating them with FLA-63, a dopamine hydroxylase inhibitor that suppresses spontaneous GH secretion without affecting the response to exogenous GRF. Blood samples are taken through the same catheter immediately prior to and 5 and 20 minutes after injections. GH levels in blood, measured by radioimmunoassay, show that synthetic [D-Leu$^{23}$, Nle$^{27}$]-rGRF(1-29)-NH$_2$ and other D-Leu$^{17}$ and D-Glu$^{25}$ analogs of rGRF are powerful stimulators of the secretion of pituitary GH and have substantially longer duration that rGRF(1-29)-NH$_2$. Other known GRF in vivo tests that are known to be effective to detect secretion of GH are used to confirm these results. Dosages between about 100 nanograms and about 50 micrograms of these peptides per Kg. of body weight are considered to be effective in causing GH secretion.

Such synthetic hpGRF analogs and possibly rGRF and pGRF analogs should be useful for human applications in which a physician wishes to elevate GH production. Stimulation of GH secretion by such analogs is of interest in patients with complete or relative GH deficiency caused by underproduction of endogenous GRF. Furthermore, it is probable that increased GH secretion and its attendant increase in growth could be obtained in humans or animals with normal GH levels. Moreover, administration should alter body fat content and modify other GH-dependent metabolic, immunologic and developmental processes. For example, these analogs may be useful as a means of stimulating anabolic processes in human beings under circumstances such as following the incurring of burns. As another example, these analogs may be administered to commercial warm-blooded animals, such as chickens, turkeys, pigs, goats, cattle and sheep, and may be used in aquiculture for raising fish and other cold-blooded marine animals, e.g. sea turtles and eels, and amphibians, to accelerate growth and increase the ratio of protein to fat gained by feeding effective amounts of the peptides.

For administration to humans, these synthetic peptides should have a purity of at least about 93% and preferably at least 98%. Purity, for purposes of this application, refers to the intended peptide constituting the stated weight % of all peptides and peptide fragments present. For the administration of such synthetic peptides to commercial and other animals in order to promote growth and reduce fat content, a purity as low as about 5%, or even as low as 0.01%, may be acceptable.

These synthetic peptides or the nontoxic salts thereof, combined with a pharmaceutically or veterinarily acceptable carrier to form a pharmaceutical composition, may be administered to animals, including humans, either intravenously, subcutaneously, intramuscularly, percutaneously, e.g. intranasally or even orally. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered to humans under the guidance of a physician, and pharmaceutical compositions will usually contain the peptide in conjunction with a conventional, solid or liquid, pharmaceutically-acceptable carrier. Usually, the parenteral dosage will be from about 100 nanograms to about 50 micrograms of the peptide per kilogram of the body weight of the host.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminal of the peptide, can be made in accordance with the known experimental practises to date to create peptides or peptide fragments that retain all or very substantial portions of the biological potency of the peptide, and such peptides are considered as being within the scope of the invention. Moreover, additions may be made to either terminal, or to both terminals, and/or generally equivalent residues can be substituted for naturally occurring residues, as is well-known in the overall art of peptide chemistry, to produce other analogs having at least a substantial portion of the potency of the claimed polypeptide without deviating from the scope of the invention.

Various features of the invention are emphasized in the claims which follow.

What is claimed is:

1. A synthetic peptide, or a nontoxic salt thereof, having the formula: H-$R_1$-$R_2$-$R_3$-Ala-Ile-Phe-Thr-$R_8$-Ser-$R_{10}$-Arg-$R_{12}$-$R_{13}$-Leu-$R_{15}$-Gln-$R_{17}$-$R_{18}$-Ala-Arg-Lys-Leu-$R_{23}$-$R_{24}$-$R_{25}$-Ile-$R_{27}$-$R_{28}$-Arg-Gln-Gln-Gly-Glu-$R_{34}$-Asn-Gln-Glu-$R_{38}$-$R_{39}$-$R_{40}$-Arg-$R_{42}$-$R_{43}$-$R_{44}$-Y wherein $R_1$ is Tyr, D-Tyr, Met, Phe, D-Phe, pCl-Phe, Leu, His or D-His having either a $C^{\alpha}$Me or $N^{\alpha}$Me substitution or being unsubstituted; $R_2$ is Ala or D-Ala; $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, Asp, D-Glu or D-Asp; $R_{27}$ is Met, D-Met, Ala, Nle, Ile, Leu, Nva or Val; $R_{28}$ is Asn or Ser; $R_{34}$ is Arg or Ser; $R_{38}$ is Gln or Arg; $R_{39}$ is Arg or Gly; $R_{40}$ is Ser or Ala; $R_{42}$ is Phe, Ala or Val; $R_{43}$ is Asn or Arg; $R_{44}$ is a natural amino acid; and Y is the radical —COOR, —CRO, —CONHNHR, —CON(R)(R') or —CH$_2$OR, with R and R' being lower alkyl, fluoro lower alkyl or hydrogen; provided however that either $R_{17}$ or $R_{23}$ is D-Leu or $R_{25}$ is either D-Glu or D-Asp and that any or all of the residues between $R_{29}$ and $R_{44}$, inclusive, may be deleted.

2. The peptide of claim 1 wherein $R_{23}$ is D-Leu.
3. The peptide of claim 1 wherein $R_{25}$ is D-Glu.
4. The peptide of claim 1 wherein $R_{27}$ is Nle.
5. The peptide of claim 1 wherein $R_{17}$ is D-Leu.
6. The peptide of claim 1 wherein $R_{25}$ is D-Asp.
7. The peptide of claim 2 wherein Y is CONH$_2$.
8. The peptide of claim 7 wherein $R_{27}$ is Nle.
9. The peptide of claim 1 wherein $R_1$ is His, $R_2$ is Ala, $R_3$ is Asp, $R_8$ is Ser, $R_{10}$ is Tyr, $R_{12}$ is Arg, $R_{13}$ is Ile, $R_{15}$ is Gly, $R_{18}$ is Tyr, $R_{24}$ is His, $R_{28}$ is Asn, $R_{34}$ is Arg, $R_{38}$ is Gln, $R_{39}$ is Arg, $R_{40}$ is Ser, $R_{42}$ is Phe, $R_{43}$ is Asn, $R_{44}$ is deleted and Y is —COOH or —CONH$_2$.
10. The peptide of claim 9 wherein $R_{17}$ is D-Leu, $R_{23}$ is D-Leu, $R_{25}$ is D-Glu, $R_{27}$ is Nle and residues 30 through 44 are deleted.
11. The peptide of claim 1 wherein $R_2$ is Ala, $R_3$ is Asp, $R_8$ is Asn, $R_{10}$ is Tyr, $R_{12}$ is Lys, $R_{13}$ is Val, $R_{15}$ is Gly, $R_{18}$ is Ser, $R_{24}$ is Gln, $R_{28}$ is Ser, $R_{34}$ is Ser, $R_{38}$ is Arg, $R_{39}$ is Gly, $R_{40}$ is Ala, $R_{42}$ is Ala, $R_{43}$ is Arg, $R_{44}$ is Leu and Y is —COOH or —CONH$_2$.
12. The peptide of claim 11 wherein $R_{17}$ is D-Leu, $R_{23}$ is D-Leu, $R_{25}$ is Asp, $R_{27}$ is Nle and residues 30 through 44 are deleted.
13. The peptide of claim 12 wherein $R_1$ is Tyr.
14. The peptide of claim 12 wherein $R_1$ is D-Tyr.

15. A pharmaceutical composition for stimulating the release of GH in an animal comprising an effective amount of the peptide of claim 1 or a nontoxic salt thereof, and a pharmaceutically or veterinarily acceptable liquid or solid carrier therefor.

16. A method for the therapeutic treatment of humans which comprises administering an effective amount of a composition in accordance with claim 15.

17. A method of stimulating the release of growth hormone in an animal, which comprises administering to said animal an effective amount of a synthetic peptide having the sequence- $R_1$-$R_2$-$R_3$-Ala-Ile-Phe-Thr-$R_8$-Ser-$R_{10}$-Arg-$R_{12}$-$R_{13}$-Leu-$R_{15}$-Gln-$R_{17}$-$R_{18}$-Ala-Arg-Lys-Leu-$R_{23}$-$R_{24}$-$R_{25}$-Ile-$R_{27}$-$R_{28}$-Arg-Gln-Gln-Gly-Glu-$R_{34}$-Asn-Gln-Glu-$R_{38}$-$R_{39}$-$R_{40}$-Arg-$R_{42}$-$R_{43}$-$R_{44}$ wherein $R_1$ is Tyr, D-Tyr, Met, Phe, D-Phe, pCl-Phe, Leu, His or D-His having either a $C^{\alpha}$Me or $N^{\alpha}$Me substitution or being unsubstituted; $R_2$ is Ala or D-Ala; $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, Asp, D-Glu or D-Asp; $R_{27}$ is Met, D-Met, Ala, Nle, Ile, Leu, Nva or Val; $R_{28}$ is Asn or Ser; $R_{34}$ is Arg or Ser; $R_{38}$ is Gln or Arg; $R_{39}$ is Arg or Gly; $R_{40}$ is Ser or Ala; $R_{42}$ is Phe, Ala or Val; $R_{43}$ is Asn or Arg; $R_{44}$ is a natural amino acid; provided however that either $R_{17}$ or $R_{23}$ is D-Leu or $R_{25}$ is either D-Glu or D-Asp and that any or all of the residues between $R_{29}$ and $R_{44}$, inclusive, may be deleted; or a nontoxic salt thereof.

18. A method for promotion of growth in warm-blooded nonhuman animals in accordance with claim 17.

19. A method for growth promotion in aquiculture by administering to fish or other cold-blooded animals in accordance with claim 17.

20. A method of accelerating growth in non-human animals, which method comprises administering an effective amount of a synthetic peptide having the sequence: $R_1$-$R_2$-$R_3$-Ala-Ile-Phe-Thr-$R_8$-Ser-$R_{10}$-Arg-$R_{12}$-$R_{13}$-Leu-$R_{15}$-Gln-$R_{17}$-$R_{18}$-Ala-Arg-Lys-Leu-$R_{23}$-$R_{24}$-$R_{25}$-Ile-$R_{27}$-$R_{28}$-$R_{29}$ wherein $R_1$ is Tyr, D-Tyr, Met, Phe, D-Phe, pCl-Phe, Leu, His or D-His having either a $C^{\alpha}$Me or $N^{\alpha}$Me substitution; $R^2$ is Ala or D-Ala; $R_3$ is Asp or D-Asp; $R_8$ is Ser, Asn, D-Ser or D-Asn; $R_{10}$ is Tyr or D-Tyr; $R_{12}$ is Arg or Lys; $R_{13}$ is Ile or Val; $R_{15}$ is Gly or D-Ala; $R_{17}$ is Leu or D-Leu; $R_{18}$ is Tyr or Ser; $R_{23}$ is Leu or D-Leu; $R_{24}$ is His or Gln; $R_{25}$ is Glu, D-Glu, D-Asp or Asp; $R_{27}$ is Met, D-Met, Ala, Nle, Ile, Leu, Nva or Val; $R_{28}$ is Asn or Ser; $R_{29}$ is Arg or des-$R_{29}$; provided however that either $R_{17}$ or $R_{23}$ is D-Leu or $R_{25}$ is either D-Glu or D-Asp.

* * * * *

UNITED STATES PATENT AND TRADEMARK OFFICE
CERTIFICATE OF CORRECTION

PATENT NO. : 4,518,586

DATED : May 21, 1985

INVENTOR(S) : Jean E. F. Rivier and Wylie W. Vale, Jr.

It is certified that error appears in the above-identified patent and that said Letters Patent is hereby corrected as shown below:

Column 4, line 16, change "is" to --as--.

Column 6, line 12, change "is" to --if--, in the first instance.

Signed and Sealed this

Twenty-sixth Day of November 1985

[SEAL]

Attest:

DONALD J. QUIGG

Attesting Officer

Commissioner of Patents and Trademarks